(12) United States Patent
Dahl

(10) Patent No.: US 6,256,534 B1
(45) Date of Patent: Jul. 3, 2001

(54) IMPLANTABLE DEFIBRILLATOR WITH COUNTERSHOCK SYNCHRONIZED TO P-WAVE

(75) Inventor: Roger Dahl, Andover, MN (US)

(73) Assignee: Angeion Corporation, Minneapolis, MN (US)

( * ) Notice: Subject to any disclaimer, the term of this patent is extended or adjusted under 35 U.S.C. 154(b) by 0 days.

(21) Appl. No.: 09/132,225

(22) Filed: Aug. 11, 1998

(51) Int. Cl.$^7$ ........................................... A61N 1/39
(52) U.S. Cl. ...................................................... 607/5
(58) Field of Search ............................ 607/5, 4; 600/518

(56) References Cited

U.S. PATENT DOCUMENTS

| Re. 36,765 | * | 7/2000 | Mehra ........................................ 607/5 |
| 4,559,946 | | 12/1985 | Mower . |
| 5,007,422 | * | 4/1991 | Pless et al. ................................ 607/5 |
| 5,074,301 | | 12/1991 | Gill . |
| 5,312,443 | | 5/1994 | Adams et al. . |
| 5,366,485 | | 11/1994 | Kroll et al. . |
| 5,366,487 | | 11/1994 | Adams et al. . |
| 5,431,687 | | 7/1995 | Kroll . |
| 5,713,924 | | 2/1998 | Min et al. . |
| 6,091,988 | * | 7/2000 | Warman et al. ........................... 607/5 |

FOREIGN PATENT DOCUMENTS 97 112555    8/1994   (WO) .

OTHER PUBLICATIONS

Suresh et al. *Synchronized Vector Peak Shocks Improve Nonthorcotomy Defibrillation Success.* Circ. 92:8; 0120, 1995.

Hsia, et al *Genesis of Sigmoidal Dose–Response Curve During Defibrillation by Random Shock: A Theoretical Model Based on Experimental Evidence for a Vulnerable Window During Ventricular Fibrillation.* PACE 13:1326–1342, 1990.

Huagui et al. *Effect of Shock Timing on Efficacy and Safety of Internal Cardioversion for Ventricular Tachycardia.* JACC 24:3:703–708, 1994.

Hsu et al. *Effect of Shock Timing on Defibrillation Success.* PACE 20:153–157, 1997.

* cited by examiner

Primary Examiner—Kennedy Schaetzle
(74) Attorney, Agent, or Firm—Patterson, Thuente, Skaar & Christensen, P.A.

(57) ABSTRACT

An implantable defibrillator for treating cardiac dysrhythmias in a human patient in which the delivery of electrical defibrillation countershocks to a plurality of implanted electrodes is synchronized to predetermined aspect of an atrial portion of the cardiac signals sensed by the device. The defibrillator includes a sealed housing structure constructed of a biocompatible material containing a battery source of electrical energy and a capacitor system to store electrical energy provided by the battery source to generate high voltage electrical countershocks. A control system within the implantable defibrillator includes sensing circuitry that senses cardiac signals representative of a heart rate and detection circuitry that evaluates the cardiac signals to detect a ventricular fibrillation. The control system includes circuitry that operates to control the storing and discharge of electric energy in the capacity system through the plurality of implanted electrodes such that delivery of the electrical energy is synchronized to a predetermined aspect of an atrial portion of the cardiac signals that is a predetermined delay after the occurrence of a P-wave.

8 Claims, 3 Drawing Sheets

IMPLANTABLE DEFIBRILLATOR WITH COUNTERSHOCK SYNCHRONIZED TO P-WAVE

FIELD OF THE INVENTION

The present invention relates to automatic cardiac defibrillation devices and especially implantable defibrillators. More particularly, the present invention relates to an automatic implantable defibrillation system in which the delivery of a ventricular countershock is synchronized to the P-wave of the sensed atrial activity of the heart.

BACKGROUND OF THE INVENTION

The field of implantable defibrillation devices is well known. Implantable defibrillators monitor cardiac signals from a patient's heart and, in response, deliver an electrical therapy or countershock in the event that a life threatening ventricular fibrillation is detected. The primary goal of any ventricular defibrillator device is to deliver a countershock that effectively defibrillates the ventricles of the heart, thereby resuscitating the patient from a life threatening condition. While it is known that defibrillation can be accomplished with energies as low as a few joules for an implantable defibrillator, these devices must be designed with the capacity to deliver electrical countershocks of significantly larger energies. There are several reasons for this design constraint, but the primary reason is that, because ventricular fibrillation is a largely chaotic condition, it can take widely different amounts of energy to defibrillate different episodes of fibrillation even in the same patient. Consequently, an implantable defibrillator must be designed to provide a maximum energy defibrillation countershock that has the greatest probability of defibrillating a patient within given parameters.

It is well known to synchronize the delivery of a cardioversion or defibrillation countershock to some aspect of the R-wave that represents the ventricular activity of the heart. If no R-wave is detected within a given time period, then the defibrillation countershock is delivered asynchronously into the heart. Examples of R-wave synchronization schemes are shown in U.S. Pat. Nos. 3,950,752, 4,384,585 and 5,193,536. One of the rationales behind synchronizing the defibrillation countershock to an R-wave is based on the idea that the R-wave as sensed by the defibrillator would represent the largest contingent of organized cells within the heart at that given moment that would not be in a refractory condition and thereby more difficult to stimulate. If this theory is correct, then synchronizing to the R-wave should be the point in time requiring the lowest energy in order to defibrillate the heart. While the theory behind this practice seems sound, the clinical experience of such wide variabilities in defibrillation thresholds when using this technique does not appear to substantiate the theory.

Other approaches to timing of delivery of a defibrillation countershock to some aspect of the R-wave signal have been proposed. In U.S. Pat. No. 5,578,062, the idea of synchronizing delivery of a defibrillation countershock to a time delay equivalent to 50% of a measured R-R interval is disclosed. In U.S. Pat. No. 5,531,767, the timing of the defibrillation pulse is synchronized to the peaks and troughs of the ECG signal as detected from a far-field detector. In U.S. Pat. No. 5,545,182, the timing of the defibrillation pulse is synchronized to a point in time at which the fibrillation ECG signal has substantially its highest amplitude and lowest frequency. Other authors have suggested synchronizing the delivery of a defibrillation countershock to various features of the sensed ventricular activity of the heart, such as the minimum or maximum derivative of the ventricular signal. Li et al., "Effect of Shock Timing on Efficiency and safety of Internal Cardioversion for Ventricular Tachycardia," JACC, Vol. 24, No. 3, Sept. 1994, pp. 703–708 (cardioversion shocks synchronized to QRS complex+100 ms); Hsu, et al., "Effect of Shock Timing on Defibrillation Success", PACE, Vol. 20, January 1997, pp. 153–157 (delivery of defibrillation shocks on upslope of ventricular signal more effective); Kuelz et al., "Integration of Absolute Ventricular Fibrillation Voltage Correlates with Successful Defibrillation", IEEE Trans. Biomed. Engr., Vol. 41, 1994, pp. 782–791 (delivery on defibrillation shocks more likely to be successful when the absolute ventricular fibrillation voltage was high than when the absolute ventricular fibrillation voltage was low). Unfortunately, all of these approaches rely on the sensed ventricular signal to provide the necessary information from which a decision will be made as to the timing of the delivery of the defibrillation countershock.

In U.S. Pat. No. 5,431,687, the idea of synchronizing delivery of a defibrillation countershock to a low value of a detected impedance of the electrode leads is disclosed. The theory behind this idea is that delivered current is responsible for effective defibrillation and the lower the measured impedance between the electrodes, the higher the delivered current will be. While this idea again seems sound in theory, to date no correlation has been established between minimum inter-electrode resistances and minimum defibrillation thresholds.

In U.S. Pat. No. 5,279,291, an atrial defibrillator is described in which delivery of an atrial defibrillation pulse is synchronized by sensing depolarization waves at a first and second area of the heart and synchronizing the atrial defibrillation pulse to the sensed depolarization waves. For an atrial defibrillator of the type described in this patent, synchronization of delivery of the atrial defibrillation pulse is critical so as not to shock into T-wave of the cardiac signal, something that is known to induce ventricular fibrillation. U.S. Pat. No. 5,403,354 improves on this technique by using a three channel sensing arrangement rather than the two channel sensing arrangement as described in the previous patent.

In U.S. Pat. No. 5,713,924, an atria defibrillator is described that treats atrial fibrillation using a high frequency, low energy pulse delivered via pacing electrodes, followed by a high energy pulse delivered via defibrillation electrodes. The delivery of this atrial therapy is synchronized to the R-wave. The patent also discusses a co-pending application in which treatment of atrial fibrillation with just a high frequency pulse burst to the atrium is synchronized to atrial depolarizations or the P-wave.

In U.S. Pat. No. 5,074,301, delivery of a ventricular cardioversion or defibrillation countershock in a dual chamber defibrillator is synchronized to a delay period following delivery of a pacing pulse to the atrium. The synchronization of the ventricular countershock based on a predetermined delay from an atrial pacing pulse is claimed to minimize post-shock atrial arrhythmias due to the possibility that the ventricular countershock was delivered during a vulnerable period in the atrium. The forced delivery of an atrial pacing pulse produces an atrial refractory period during which the atrium is not susceptible to atrial arrhythmias.

While the goal of reducing defibrillation thresholds in terms of the maximum energy required for consistently successful ventricular defibrillation is a long recognized goal, the existing techniques for synchronizing the delivery of ventricular defibrillation countershocks could be improved upon to decrease the variability of energy required for successful defibrillation.

SUMMARY OF THE INVENTION

The present invention is an implantable defibrillator for treating cardiac dysrhythmias in a human patient in which the delivery of electrical defibrillation countershocks to a plurality of implanted electrodes is synchronized to a predetermined aspect of an atrial portion of the cardiac signals sensed by the device. The implantable defibrillator includes a sealed housing structure constructed of a biocompatible material containing a battery source of electrical energy and a capacitor system to store electrical energy provided by the battery source to generate high voltage electrical countershocks. A control system within the implantable defibrillator includes sensing circuitry that senses cardiac signals representative of a heart rate and detection circuitry that evaluates the cardiac signals to detect a ventricular fibrillation. The control system includes circuitry that operates to control the storing and discharge of electric energy in the capacitor system through the plurality of implanted electrodes such that delivery of the electrical energy is synchronized to a predetermined aspect of an atrial portion of the cardiac signals.

Preferably, the sensing circuitry is connected to a first set of implanted electrodes for sensing the atrial portion of the cardiac signals and to a second set of implanted electrodes for sensing a ventricular portion of the cardiac signals. The present invention takes advantage of the information about the primary QRS complex from the atrial channel to synchronize the delivery of a ventricular defibrillation pulse. Instead of trying to synchronize delivery of a defibrillation countershock to some aspect of the ventricular signal, the present invention relies on the atrial signal to serve as the yardstick by which the timing of the delivery of a defibrillation countershock will be measured. Preferably, the predetermined aspect of the atrial cardiac signal is a predetermined delay after the occurrence of a P-wave. This predetermined delay may be based on a measured delay between at least one P-wave and one R-wave occurring prior to detection of the ventricular fibrillation. In the context of a dual chamber device, the measured delay may be an aspect of an A-V delay calculated by the implantable defibrillator for purposes of dual chamber pacing.

DETAILED DESCRIPTION OF THE PREFERRED EMBODIMENT

Figure 1:
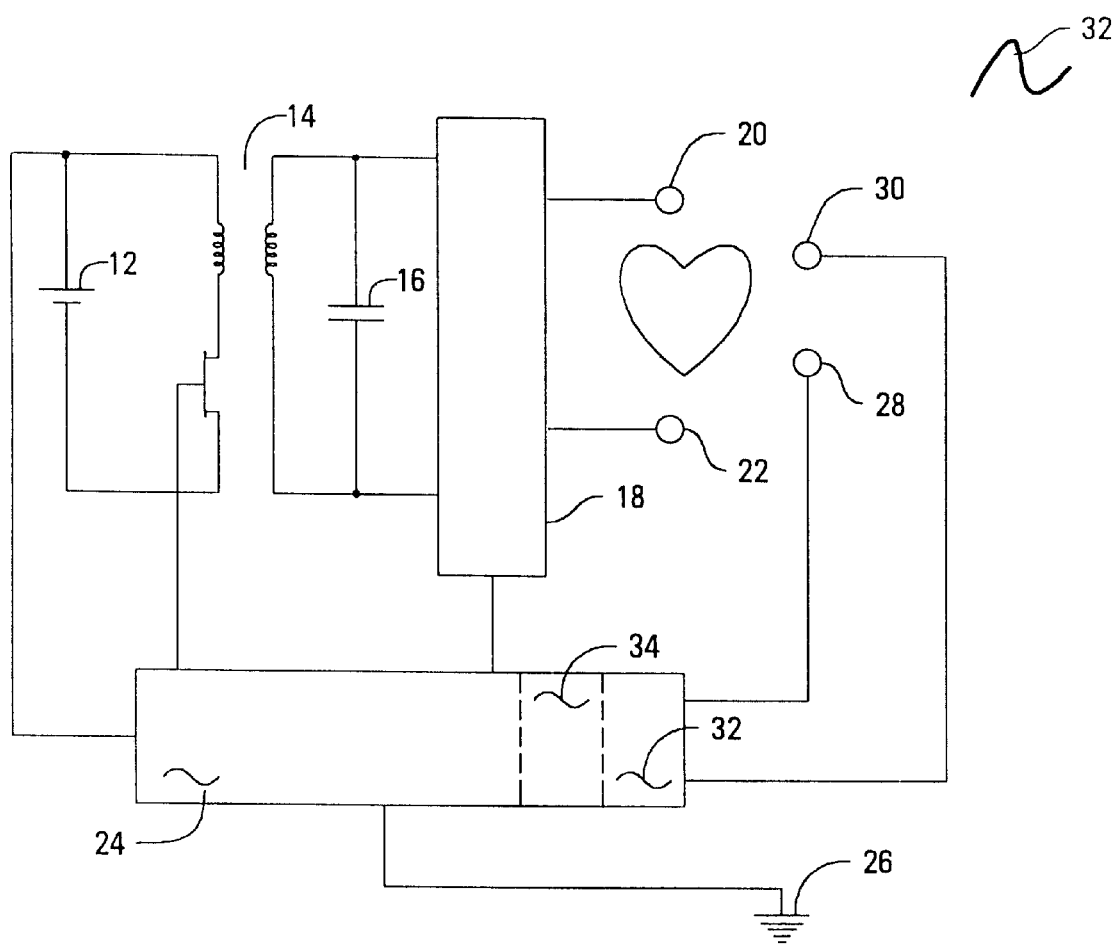
FIG. 1 is a simplified circuit diagram of an implantable defibrillator system.

Referring now to FIG. 1, a simplified circuit diagram of an implantable defibrillator system 10 in accordance with a preferred embodiment of the present invention is shown. Implantable defibrillator system 10 includes a battery system 12 connected to a high voltage transformer 14 for developing a high voltage across transformer 14 which is then applied to a capacitor system 16. The high voltage capacitor system 16 stores an electrical charge which is then selectively discharged through an output switching network 18 into electrodes 20, 22 as an electrical countershock for treating ventricular dysrhythmias. A control system 24, preferably a microcontroller or microprocessor with appropriate software and memory, is connected to the battery system 12, high voltage transformer 14 and output switching network 18 to control the charging and discharging of the electrical countershock. Control system 24 preferably includes telecommunication circuitry 26 for communicating external to the patient in which implantable defibrillator system 10 is implanted, as well as sensing electrodes 28, 30 and sensing circuitry 32 and detection circuitry 34 for detecting a ventricular dysrhythmias. It will be understood that the details and construction of implantable defibrillator system 10 may be understood by reference to known implantable defibrillator systems, such as described in U.S. Pat. No. 5,405,363 or implantable defibrillator systems which are commercially available. While the present invention is directed to an implantable defibrillator system 10 capable of performing ventricular defibrillation, it will be recognized that the implantable defibrillator system 10 may also be capable of providing other cardiac stimulation outputs, such as single chamber pacing, dual chamber pacing, anti-tachycardia pacing, ventricular cardioversion and atrial cardioversion and defibrillation.

Preferably, sensing electrodes 28 and 30 are each comprised of a pair of bipolar or unipolar electrodes, with sensing electrodes 28 positioned to receive signals from the right ventricle (RV) and sensing electrodes 30 positioned to receive signals from the right atrium (RA). In this way, two separate cardiac signals are detected, one for the atrial cardiac signal and one for the ventricular cardiac signal. Alternatively, but less preferably, a single set of sensing electrodes 30 may be used to sense both the ventricular and atrial cardiac signals with the detection circuit 34 utilizing morphology algorithms or the like to discriminate the atrial cardiac signals from the ventricular cardiac signals in the same channel. As will be discussed in further detail, however, such a single channel sensing configuration may reduce the advantages of the dual channel sensing of the preferred embodiment. It will also be recognized that other sensing electrode positions may be used in accordance with the present invention; or that even other types of sensors, such as physiological sensors or pressure sensors, may be used in accordance with the present invention as long as the electrical cardiac activity of the heart is extractable from the output of such a sensor.

Figure 2:
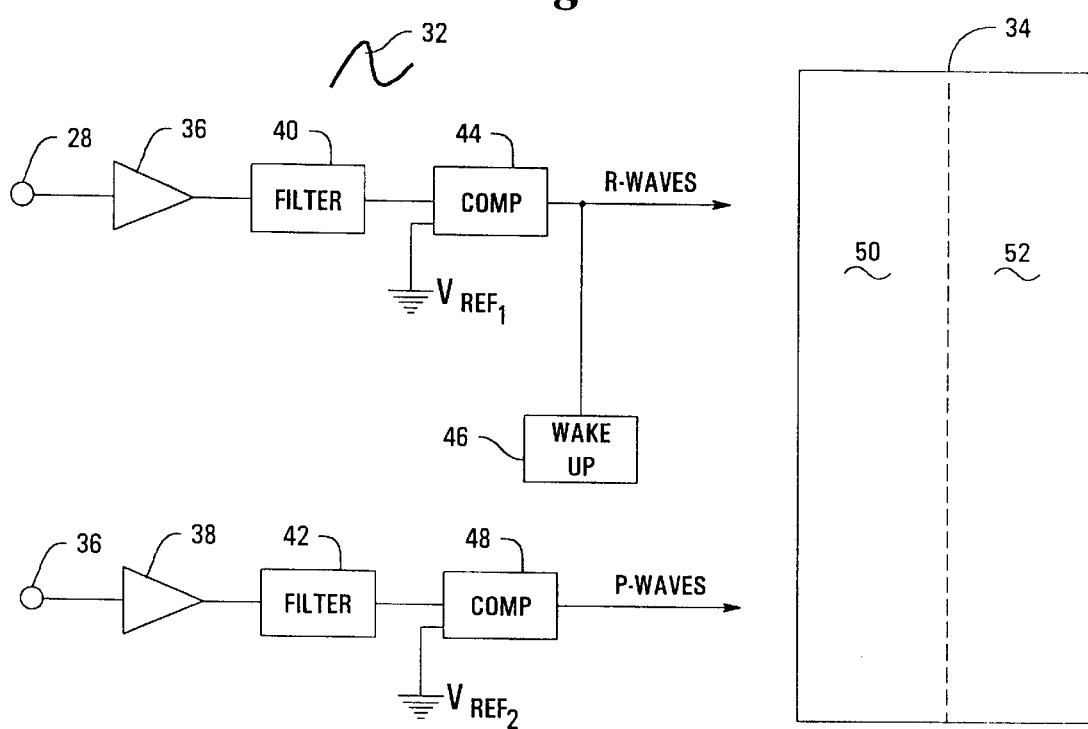
FIG. 2 is a simplified circuit diagram of a preferred embodiment of the sensing circuitry and detection circuitry of the present invention.

Referring now to FIG. 2, a simplified circuit diagram of the preferred embodiment of sensing circuitry 32 and detection circuitry 34 is shown. Typically, very weak cardiac signals are detected across the electrodes 28 and 30 that are electrically connected to an amplifier circuit 36, 38 that amplifies each channel of the cardiac signals. Sensing circuitry 32 preferably also includes circuitry 40, 42 to filter the cardiac signals. Preferably, the ventricular channel output of amplifier circuits 36 and filter circuitry 40 is then processed by a comparator circuit 44 to detect the occurrence of each R-wave in the cardiac signal which is representative of a ventricular contraction or heart beat. The output of comparator circuit 44 is sent to detection circuitry 34 and, in a preferred embodiment to wakeup circuit 46. The atrial channel output of amplifier circuit 38 and filter circuit 42 is also processed by a comparator circuit 48 to detect the occurrence of each P-wave in the atrial channel of the cardiac signals. Again, the output of comparator circuit 48 is preferably processed by detection circuitry 34.

In the case of the preferred embodiment, detection circuitry 34 is implemented in the data memory 50 and software 52 of a microprocessor, preferably the same microprocessor that serves as the control system 18. In order to conserve the power consumed by this microprocessor, a wakeup circuit 46 may be implemented to determine the various conditions under which the microprocessor should be powered up to process the cardiac signals. Although detection circuitry 34 is shown as being implemented by a programmed microprocessor, it will be recognized that it is also possible to implement detection circuitry 34 utilizing individual circuit and logic components fabricated on an integrated circuit, for example.

Figure 3:
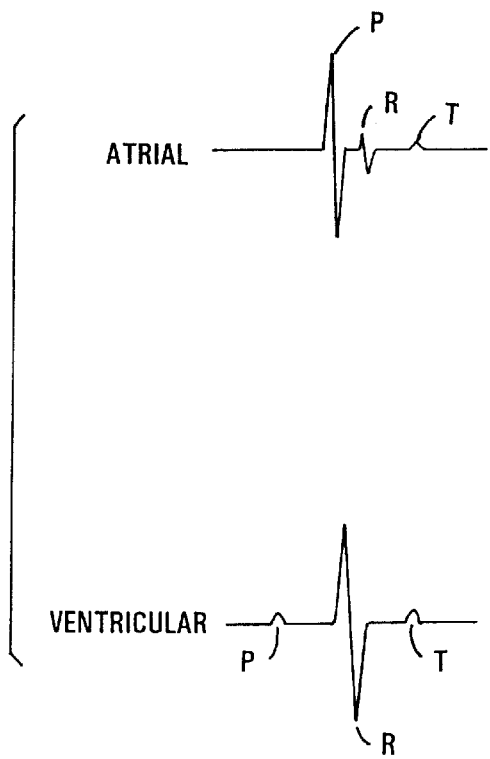
FIG. 3 is a graphical representation of both the atrial and ventricular channels of a cardiac signal during normal sinus rhythm.
Figure 4:
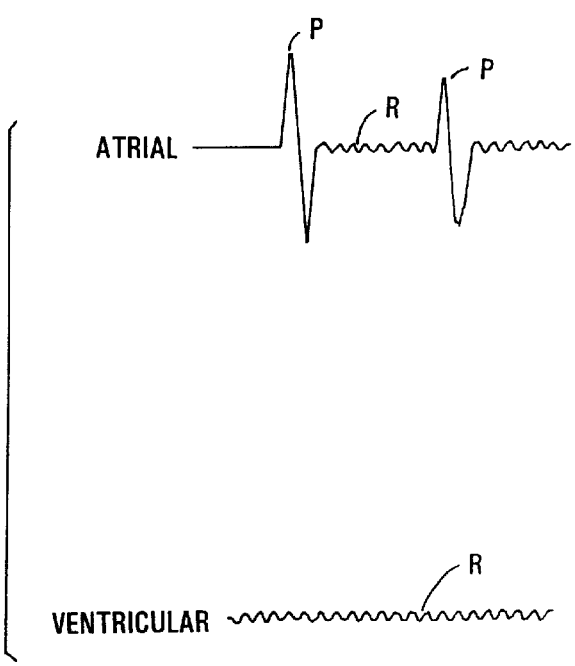
FIG. 4 is a graphical representation of the both the atrial and ventricular channels of a cardiac signal during ventricular fibrillation.

The relationship between the atrial channel and the ventricular channel of the cardiac signal is well known, particularly in the art of dual chamber pacemakers and dual chamber defibrillators. FIG. 3 shows a typical cardiac signal output from both the atrial channel and the ventricular channel. It can be seen that although the standard QRS complex is present in both channels, in the atrial channel, the P-wave is more prominent, whereas in the ventricular channel, the R-wave plainly dominates the output. During ventricular fibrillation, however, the R-wave will diminish to as little as 30% of its normal amplitude and, due to the presence of potentially multiple reentry loops that may be causing the arrhythmia, the presence of R-waves in the ventricular cardiac signal may be dispersed and overlapping as shown in FIG. 4.

It has been found that due to the point source location of the sensing electrodes 28 in a bipolar configuration typically in the apex of the right ventricle, the ventricular channel tends to represent the activation front of the QRS complex in that particular localized region of the right ventricle. While there may be times when this localized region is very representative of activation state of the majority of ventricular tissue, given the chaotic nature of ventricular fibrillation and especially in the event that the ventricular fibrillation is due to multiple reentrant activation loops, it is also likely that the ventricular channel may be picking up on the R-wave information for a localized area which is not representative of the activation state of the vast majority of ventricular tissue. Because of the separation between the atrial and ventricular cardiac electrical activity as regulated by the AV node, most ventricular fibrillations do not immediately cause the atrium to begin fibrillation as well. Consequently, as seen in FIG. 4, while the R-waves are no longer disconcernable in either channel, the atrial channel of the cardiac signal continues to exhibit R-waves which track what would have otherwise been the QRS complex that the heart was exhibiting just prior to ventricular fibrillation.

The present invention takes advantage of the information about the primary QRS complex from the atrial channel to synchronize the delivery of a ventricular defibrillation pulse. Instead of trying to synchronize delivery of a defibrillation countershock to some aspect of the ventricular signal, the present invention relies on the atrial signal to serve as the yardstick by which the timing of the delivery of a defibrillation countershock will be measured. Preferably, the predetermined aspect of the atrial cardiac signal is a predetermined delay after the occurrence of a P-wave. This predetermined delay may be based on a measured delay between at least one P-wave and one R-wave occurring prior to detection of the ventricular fibrillation. In the context of a dual chamber device, the measured delay may be an aspect of an A-V delay calculated by the implantable defibrillator for purposes of dual chamber pacing. Alternatively, the aspect of the atrial signal that is used for synchronization could be some measurement of amplitude, slope or organizational attribute of the atrial signal By using separate channels for the atrial signals and the ventricular signals, the localized point source phenomenon that has been observed with respect to synchronizing defibrillation countershocks to some aspect of the sensed ventricular signal can be avoided. Recently, implantable defibrillators have been developed with signal processing morphology that is used to discriminate atrial signals from ventricular signals on a single ventricular sense channel. The purpose of using this type of signal morphology is to decrease the incidence of inappropriate shock delivery due to confusion between atrial fibrillation (AF) or supraventricular tachycardia (SVT) from ventricular fibrillation (VF). In the context of the present invention, it will be recognized that a similar signal morphology technique may also be used to extract an atrial signal the single ventricular sense channel. Because the present invention relies on the atrial signal, the use of such morphology techniques must be modified to retain, rather than discard or filter, the atrial signal. Once the atrial signal has been retained, the present invention can be implemented in the manner describe above with respect to a dual channel sensing system.

I claim:

1. An implantable defibrillator for treating cardiac dysrhythmias in a human patient by delivering electrical countershocks to a plurality of implanted electrodes, the implantable defibrillator comprising:

a sealed housing structure constructed of a biocompatible material;

a battery source of electrical energy contained in the housing;

a capacitor system operably connected to the battery source to store electrical energy provided by the battery source to generate high voltage electrical countershocks;

a control system operably connected to the battery source and the capacitor system, including sensing circuitry that senses cardiac signals representative of a heart rate;

detection circuitry operably connected to the sensing circuitry that evaluates the cardiac signals to detect a ventricular fibrillation; and control circuitry operably connected to the detection circuitry and the sensing circuitry that controls the storing and discharge of electric energy in the capacitor system through the plurality of implanted electrodes such that delivery of the electrical energy is synchronized to a predetermined aspect of an atrial portion of the cardiac signals that is a predetermined delay after the occurrence of a P-wave.

2. The implantable defibrillator of claim 1 wherein the predetermined delay is based on a measured delay between at least one P-wave and one R-wave occurring prior to detection of the ventricular fibrillation.

3. The implantable defibrillator of claim 2 wherein the measured delay is an aspect of an A-V delay calculated by the implantable defibrillator for purposes of dual chamber pacing.

4. The implantable defibrillator of claim 1 wherein the sensing circuitry is connected to a first set of implanted electrodes for sensing the atrial portion of the cardiac signals and to a second set of implanted electrodes for sensing a ventricular portion of the cardiac signals.

5. A method of operating an implantable defibrillator for treating cardiac dysrhythmias in a human patient, the implantable defibrillator including a sealed housing structure constructed of a biocompatible material containing a battery source of electrical energy, a high voltage capacitor system and a control system which cooperate to deliver electrical countershocks to a plurality of implanted electrodes, the method comprising:

sensing cardiac signals representative of a heart rate;

using the control system to evaluate the cardiac signals to detect a ventricular fibrillation; and delivering an electrical countershock through the implanted electrodes in response to detection of the ventricular fibrillation such that delivery of the electrical energy is synchronized to a predetermined aspect of an atrial portion of the cardiac signals that is a predetermined delay after the occurrence of a P-wave.

6. The method of claim 5 further comprising the step of measuring a delay between at least one P-wave and one R-wave occurring prior to detection of the ventricular fibrillation as the predetermined delay.

7. The method of claim 5 further comprising the step of calculating an A-V delay for purposes of dual chamber pacing and utilizing some aspect of the A-V delay as the predetermined delay.

8. The method of claim 5 wherein the step of sensing the cardiac signals is accomplished by utilizing a first set of implanted electrodes for sensing the atrial portion of the cardiac signals and by utilizing a second set of implanted electrodes for sensing a ventricular portion of the cardiac signals.

* * * * *